US00PP09975P

United States Patent [19]

Anderson

[11] Patent Number: Plant 9,975

[45] Date of Patent: Jul. 22, 1997

[54] BLACK CURRANT PLANT NAMED 'BEN CONNAN'

[75] Inventor: Malcolm M. Anderson, Dundee, Scotland

[73] Assignee: Scottish Crop Research Institute, Dundee, Scotland

[21] Appl. No.: 651,394

[22] Filed: May 22, 1996

[51] Int. Cl.[6] ..... A01H 5/00

[52] U.S. Cl. ..... Plt./33.1

[58] Field of Search ..... Plt./33.1

[56] References Cited

PUBLICATIONS

"RAPD fingerprinting of blackcurrant (*Ribes nigrum L.*) cultivars", P.G. Lanham et al., *Theor. Appl. Genet.*, vol. 90, pp. 166 to 192 (1995).

*Primary Examiner*—James R. Feyrer

*Attorney, Agent, or Firm*—Burns, Doane, Swecker & Mathis, L.L.P.

[57] ABSTRACT

A new and distinct cultivar of black currant (i.e., *Ribes nigrum* L.) is provided. The cultivar forms attractive very large deep black glossy berries in good yields that are amenable to mechanical harvesting. A vigorous and compact growth habit commonly is exhibited. A cup-shaped plant commonly is formed wherein slightly fewer branches are present at the center. The new cultivar flowers early and the berries mature early. Good resistance to American gooseberry mildew is exhibited. The new cultivar is well suited for consumption when freshly picked or can be canned to form jams, preserves, conserves, etc.

4 Drawing Sheets

SUMMARY OF THE INVENTION

The new black currant (i.e., *Ribes nigrum* L.) cultivar of the present invention was created during the course of a planned breeding program carried out during 1978 at the Scottish Crop Research Insitutue, Dundee, Scotland. The female parent (i.e., the seed parent) was the 'Ben Sarek' cultivar (non-patented in the United States). The male parent (i.e., the pollen parent) was the 'Ben Lomond' cultivar (non-patented in the United States). The parentage of the new cultivar can be summarized as follows:

'Ben Sarek'×'Ben Lomond'.

The original plant of the new cultivar was selected from the plants resulting from this cross and was found to exhibit:

(a) an early flowering propensity,
(b) a vigorous and compact growth habit capable of forming a cup-shaped plant with slightly fewer branches at the center that is amenable to mechanical fruit harvest.
(c) the ability to bear very large glossy deep black fully-ripened berries of good quality in high yields that mature early in the season and are particularly well suited for fresh consumption or for canning, and
(d) exhibits good resistance to American gooseberry mildew.

When compared to the parent 'Ben Lomond' cultivar, the new cultivar of the present invention commonly flowers approximately 2 to 3 days earlier, the berries commonly ripen approximately 4 to 5 days earlier, the plant is more compact, the leaves are a paler green and less rugose, the petioles bear anthocyanin coloration only at the base, and the berries commonly are larger.

The new cultivar can be grown to advantage while employing a standard planting density of approximately 7,400 plants/hectare. Ease of management is provided since the new cultivar commonly requires a reduced need for autumn pruning.

The new cultivar has been asexually reproduced by hardwood cuttings, softwood cuttings, single bud cuttings, and tissue culture at the Scottish Crop Research Institute, Dundee, Scotland. Such asexual reproduction has demonstrated that the characteristics of the new cultivar are stable and are transmitted without change through succeeding propagations. Additionally, the performance of the new cultivar has been evaluated at the National Fruit Trials held at Brogdale Experimental Horticulture Station, Faversham, Kent, United Kingdom, and at the institute of Horticultural Plant Breeding, Balsgard, Sweden.

The new cultivar of the present invention has been named the 'Ben Connan' cultivar.

When plant material of the 'Ben Connan' cultivar is subjected to RAPD fingerprinting using primer OPA-o6, GGTCCCTGAC, it is found to exhibit a bandmap which conforms its genetic distinctiveness as described in "RAPD fingerprinting of blackcurrant (*Ribes nigrum* L.) cultivars," by P.G. Lanham, R. M. Brennan, C. Hacket, and R.J. McNicol, appearing in *Theor. Appl. Genet.*, vol. 90, pp. 166 to 172 (1995), which is herein incorporated by reference.

BRIEF DESCRIPTION OF THE PHOTOGRAPHS

The accompanying photographs show typical specimens of the new cultivar in color as true as is reasonably possible to make the same in color illustrations of this character. The plants had been asexually reproduced by hardwood cuttings and were grown outdoors in breeding plots of the Scottish Crop Research Insitutute located at Dundee, Scotland.

FIG. 1 illustrates young (one year-old) vegetative stems of the new cultivar wherein leaf morphology and the initial growth characteristics are apparent. The actual leaf coloration tends to be somewhat less vivid than that shown in FIG. 1 and corresponds more accurately to that shown in FIGS.

2 and 3 and as described hereafter with reference to The R.H.S. Colour Chart.

FIG. 2 illustrates a typical mature fruiting bush of three years of age when observed during late July. The compact growth habit and cropping potential of the new cultivar are apparent.

FIG. 3 illustrates on the left a typical fruiting stem of the new cultivar of the present invention and on the right for comparative purposes a typical fruiting stem of the previously available 'Baldwin' cultivar (non-patented in the United States). The mode of fruit presentation and the relative fruit size are apparent with generally larger berries being borne by new cultivar of the present invention.

FIG. 4 illustrates the very large and attractive shiny deep black berries of the new cultivar while present in a glass for display purposes. Such glass shown in the photograph has a mouth diameter of approximately 7.5 cm.

DETAILED DESCRIPTION

Figure 1:
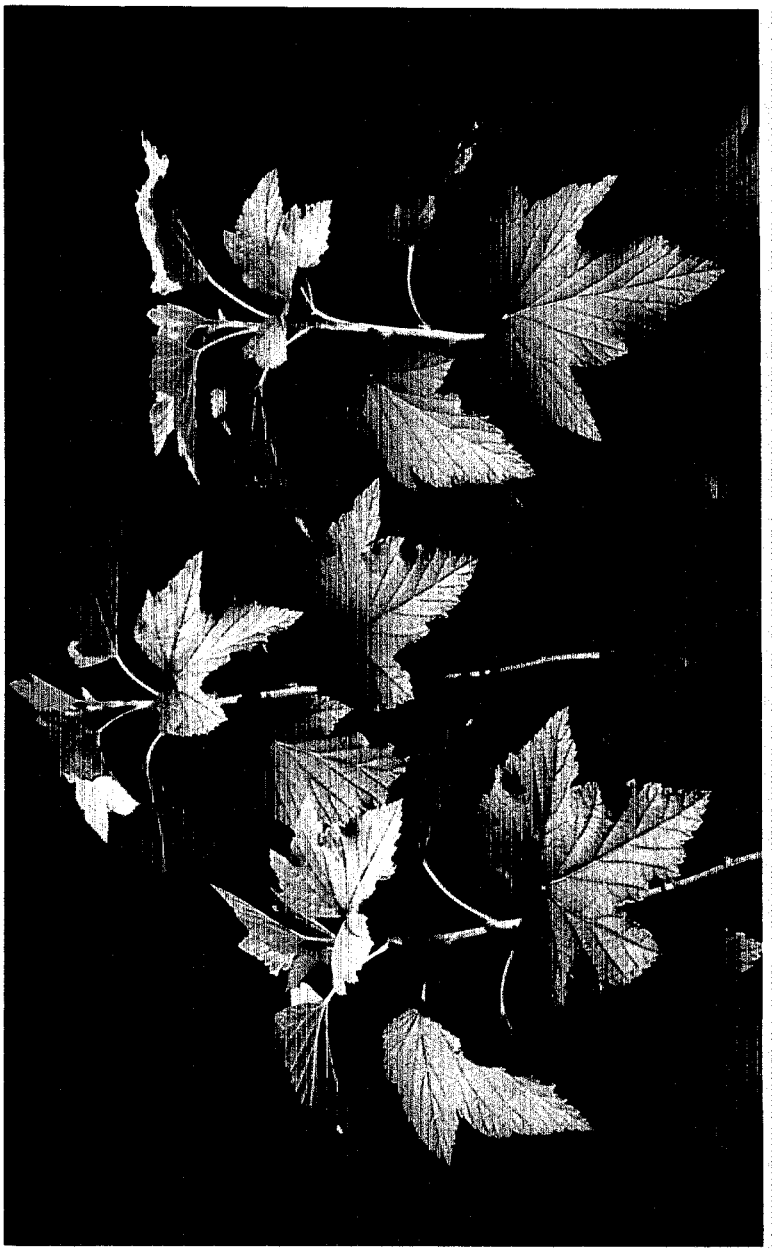

The following is a detailed descriptionof the new cultivar. The specimens described were grown at the Scottish Crop Research Institute, Dundee, Scotland, and at the National Fruit Trials held at the Brogdale Experimental Horticulture Station, Faversham, Kent, United Kingdom. The chart used in the identification of colors is that of The Royal Horticultural Society (R.H.S. Colour Chart). Other color terms are to be accorded their customary dictionary significance.

Plant:

*Growth habit.*—The growth habit is compact (as illustrated). The overall growth habit tends to be cup-shaped with the branches tending to grow outwards with the presence of a slightly fewer number of branches at the center of the bush as the season proceeds. The branches tend to bend over when carrying a full fruit crop, but substantially return to their original position following harvest.

*Dimensions.*—Commonly approximately 0.8 m. in height and approximately 0.6 m. in width for a three year-old bush. Generally shorter in stature than other commercial cultivars.

*Basal shoots.*—Numerous.

*Vigor.*—Strong with sturdy erect shoots are formed in moderate to high numbers.

Leaves:

*Leaf coloration.*—Spinach Green, commonly approaches Green Group 137B, with some variation depending on specific growing conditions encountered. The coloration commonly is a paler green than that of the 'Ben Lomond' cultivar.

*Leaf apearance.*—Medium to strong glossiness on the upper surface.

*Leaf configuration.*—The base of the blade is open, the midrib is slightly recurved, and the terminal lobe is medium-sized. The leaves tend to be less rugose than those of the 'Ben Lomond' cultivar.

*Leaf size.*—Medium, and typically approximately 13 cm.×13 cm. when mature.

*Petiole coloration.*—Lettuce Green, approaches Yellow-Green Group 144A, with some variation, and with occasional weak anthocyanin coloration only at the base unlike the 'Ben Lomond' cultivar.

*Petiole surface.*—Sparse or lacking in pubescence.

*Stem coloration.*—Shades of dark brown (as illustrated).

Flowers:

*Bud color.*—Scheele's Green, Green Group 143A, with some variation. Overwintering buds commonly show strong anthocyanin coloration and a strong bloom.

*Flowering date.*—Early; approximately April 25th for full flower at Kent, United Kingdom; and approximately 2 to 3 days prior to the 'Ben Lomond' cultivar. The exact flowering time for a given season is dependent upon the environmental conditions encountered.

*Flower coloration.*—Off-white, with weak anthocyanin coloration on the sepal and ovary.

*Flower racemes.*—Short and comonly one per node.

*Flower ferquency.*—Commonly produced one raceme per bud with approximately 5 to 7 flowers on a primary raceme.

Fruit:

*Size.*—Very large and generally larger than that of the 'Baldwin' and 'Ben Lomond' cultivars. For instance, approximately 187 berries of the new cultivar weigh 250 grams, compared to approximately 206 berries of the 'Ben Lomond' cultivar.

*Taste.*—Pleasant with an acid-sweet flavor.

*Configuration.*—Round.

*Consistency.*—Firm.

Figure 2:
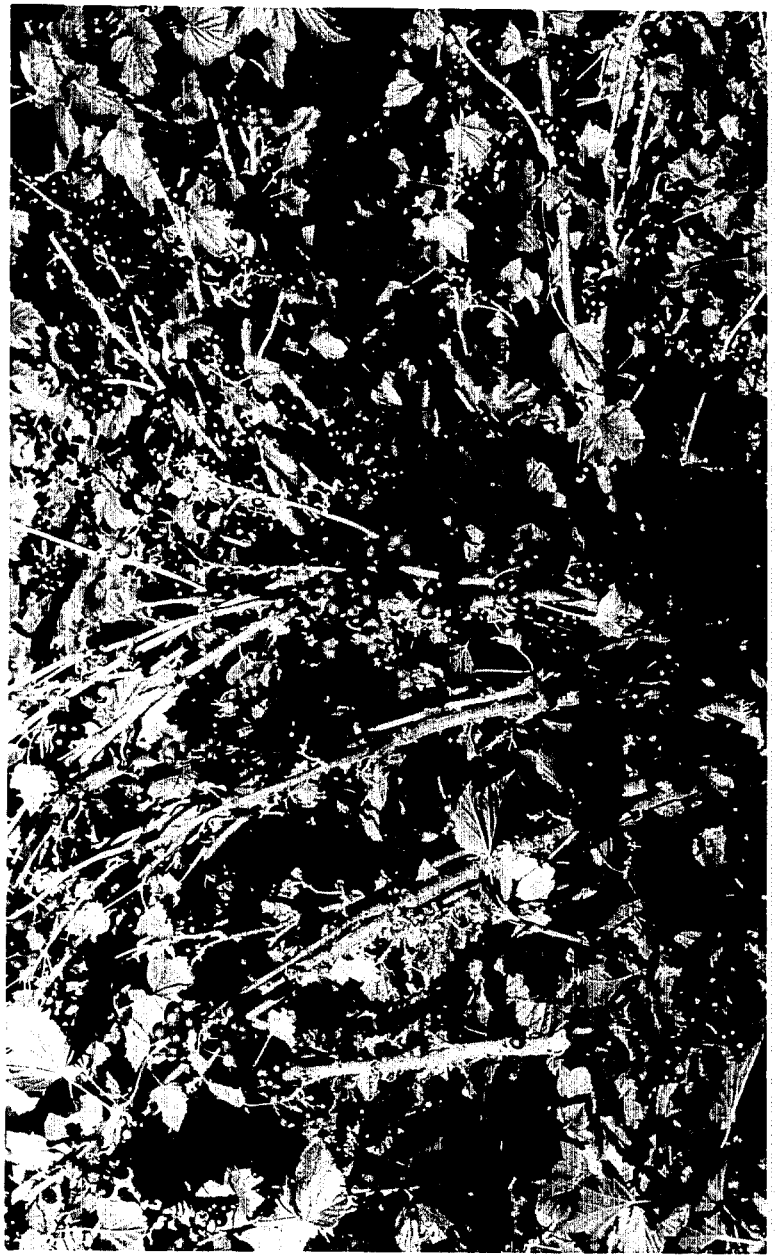
Figure 3:
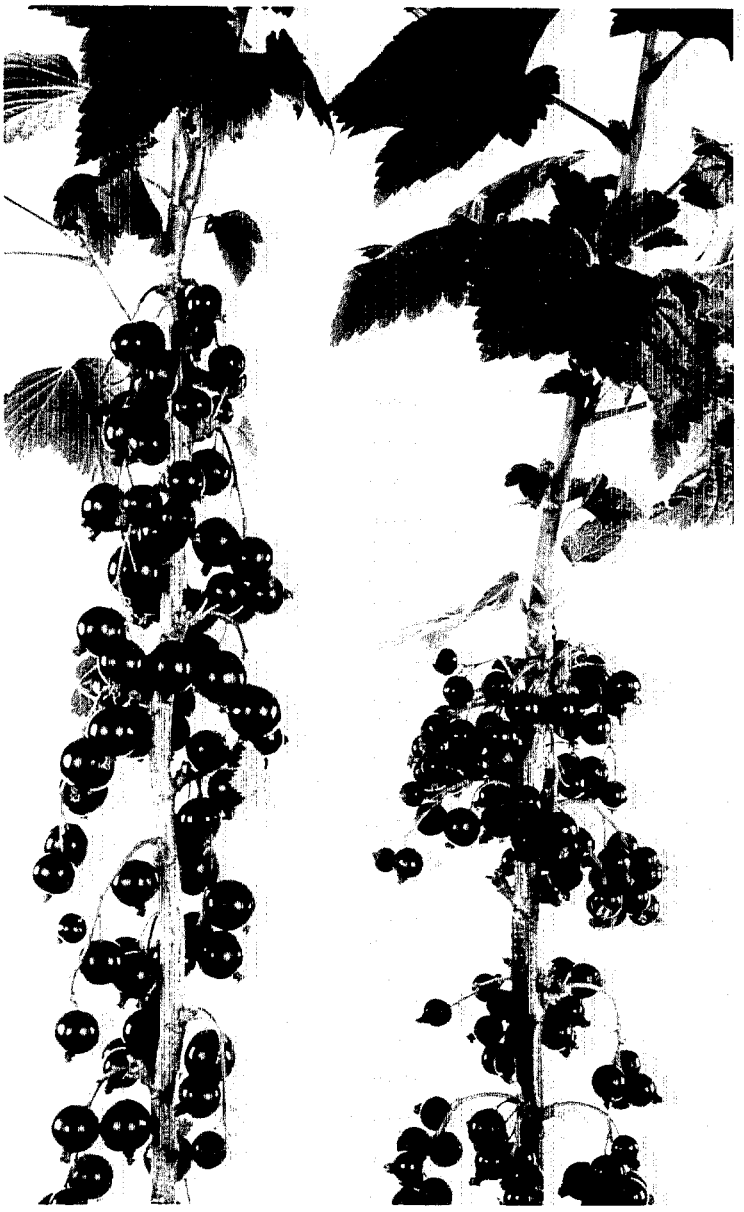
Figure 4:
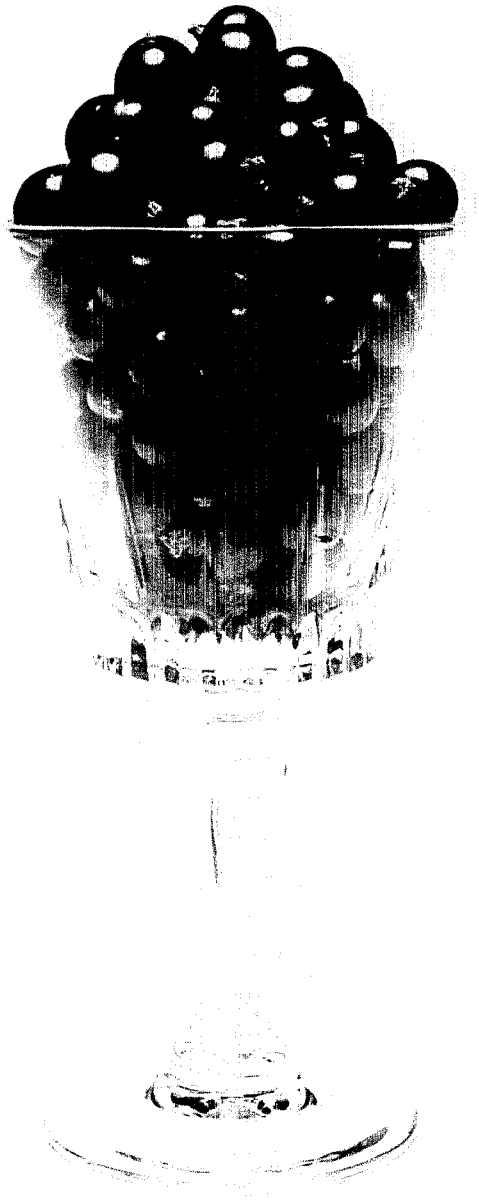

*Appearance.*—Glossy, and deep black that approaches Black Group 202A when fully ripe. The fruit coloration varies with the stage of ripeness as illustrated in FIG. 2. The fruit is attractive and well presented on the bush.

*Fruit ripening.*—Early. Was harvested July 18th at Kent, United Kingdom. This is approximately 4 to 5 days prior to the 'Ben Lomond' cultivar and approximately 6 days later than the 'Ben Sarek' cultivar at the same location. Also, the ripening tends to be more even and uniform than that of the 'Ben Lomond' cultivar. The ripening date in a given season is influenced by environmental conditions that are encountered.

*Anthocyanin content.*—Using spectrophotometry at an absorbance of 515 nm. the value was fairly low at approximately 0.5. This compares to approximately 0.968 for the 'Ben Lomond' cultivar.

*Ascorbic acid content.*—130 mg./100 g. This compares to 119 mg./100 g. for the 'Ben Lomond' cultivar. Accordingly the new cultivar is superior to the 'Ben Lomond' cultivar with respect to ascorbic acid content.

*Yields.*—High yields, typically approximately 17 tonnes/hectare on average at most locations where testing has been carried out.

*Management and harvesting.*—Suitable for machine picking and can be agronomically managed using conventional growing conditions with a reduced need for autumn pruning.

*Market.*—Excellent for consuming while fresh or for canning to produce jams, preserves, conserves, etc.. The fruit is not ideally suited for juice production. Ideal for growing my home gardeners or for growing commercially while providing consumers an opportunity to pick the berry crop.

Disease and pest resistance: Good resistance to American gooseberry mildew (i.e., *Sphaerotheca morsuvae*) and leaf-curling midge (i.e., *Dasineura tetensi*). Average susceptibility to other black currant pests and diseases.

Resistance to cold: Good tolerance to winter temperatures throughout Europe has been observed as well as reasonable tolerance to spring frosts.

I claim:

1. A new and distinct variety of black currant plant having the following combination of characteristics:

(a) an early flowering propensity,
(b) a vigorous and compact growth habit capable of forming a cup-shaped plant with slightly fewer branches at the center that is amenable to mechanical fruit harvest,
(c) the ability to bear very large glossy deep black fully-ripened berries of good quality in high yields that mature early in the season and are particularly well suited for fresh consumption or for canning, and
(d) exhibits good resistance to American gooseberry mildew;

substantially as herein shown and described.

* * * * *